United States Patent [19]

Leung et al.

[11] Patent Number: 4,979,393
[45] Date of Patent: Dec. 25, 1990

[54] PROCESS FOR RAPIDLY DETERMINING THE SOLIDS CONTENT IN DRILLING FLUIDS

[75] Inventors: Peter K. Leung, Sugar Land; Ronald P. Steiger, Houston, both of Tex.

[73] Assignee: Exxon Production Research Company, Houston, Tex.

[21] Appl. No.: 398,352

[22] Filed: Aug. 24, 1989

[51] Int. Cl.$^5$ .............................................. E21B 49/00
[52] U.S. Cl. ....................................... 73/155; 324/376
[58] Field of Search .................. 73/53, 61.4, 151, 153, 73/155; 166/267; 324/376, 377; 436/30, 31

[56] References Cited

U.S. PATENT DOCUMENTS

| | | | |
|---|---|---|---|
| 4,369,655 | 1/1983 | Scearce | 73/153 |
| 4,370,885 | 2/1983 | Alekhin et al. | 73/153 |
| 4,876,512 | 10/1984 | Kroeger et al. | 73/153 |
| 4,878,382 | 11/1989 | Jones et al. | 73/153 |

OTHER PUBLICATIONS

Van Olphen, H., "An Introduction to Clay Colloid Chemistry", Wiley-Interscience, New York, 1977, Chapter 5.
American Petroleum Institute Publication RP 13B, "API Recommended Practice Standard Procedure for Field Testing Drilling Fluids", Eleventh Edition, May 1, 1985, pp. 13–15.
Theng, B. K. G., "The Chemistry of Clay-Organic Reactions", John Wiley & Sons, New York, 1974, Chapter 3.
Jaynes, W. F. and Bigham, J. M., "Multiple Cation-Exchange Capacity Measurements on Standard Clays Using a Commercial Mechanical Extractor", Clays and Minerals, 1986, vol. 34, No. 1, pp. 93–98.
Raythatha, R. and Sen, P. N., "Dielectric Properties of Clay Suspensions in the MHz to GHz Range", Journal of Colloid and Interface Science, Feb. 1986, vol. 109, No. 2, pp. 301–309.
Shen, L. C., "Problems in Dielectric-Constant Logging and Possible Routes to their Solutions", The Log Analyst, 1985, Nov.–Dec., pp. 14–25.
Wharton, R. P., et al., "Electromagnetic Propagation Logging: Advances in Technique and Interpretation", 55th Ann. Fall Tech. Conf., Dallas, Texas, Sep. 21–24, 1980, SPE Paper 9267.
Lockhart, N. C., "Electrical Properties and the Surface Characteristics and Structure of Clays", Journal of Colloid and Interface Science, 1980, vol. 74, No. 2, pp. 509–519.
Weiler, R. A. and Chaussidon, J., "Surface Conductivity and Dielectric Properties of Montmorillonite Gels", Clay and Minerals, 1968, vol. 16, pp. 147–155.

*Primary Examiner*—John Chapman
*Assistant Examiner*—Kevin D. O'Shea
*Attorney, Agent, or Firm*—Raul R. Montes

[57] ABSTRACT

A method for determining at wellsites the solids content of drilling fluids by high-frequency dielectric measurements including: preparing samples of the drilling fluid, of the drill cuttings from the formation, and of each solids-additives type added to the drilling fluid for uniform dielectric constant measurements at preselected frequencies and obtaining the solids content in accordance with the relationship between the dielectric constant measurements of the drilling fluid-solids, drill cuttings, and each of the solids-additives type. In accordance with the method of the invention two levels of determination are possible. These levels of determination depend upon whether the quantities of solids-additives type added to the drilling fluid are known.

11 Claims, 1 Drawing Sheet

PROCESS FOR RAPIDLY DETERMINING THE SOLIDS CONTENT IN DRILLING FLUIDS

FIELD OF THE INVENTION

This invention pertains to a method for determining the solids content in drilling fluids by high-frequency dielectric constant measurements.

BACKGROUND OF THE INVENTION

The determination of the solids content in drilling fluids (drilling "muds") is important in the drilling for hydrocarbons. Properties of drilling fluids such as density, viscosity, gel strength, and filtration rate depend to a considerable extent on the solids content of the drilling fluid. As the solids content increases, the drilling fluid density (or "mud weight") also increases, and mud weight has a direct effect on drilling rates. The viscosity of drilling fluids is affected by the relative quantity of solids present, and knowledge of this quantity may afford an explanation of certain undesirable properties and indicate the treatment to be used. For example, if the solids content of a thick water-base drilling fluid is excessive, water instead of chemicals should be used to thin the drilling fluid. Improper solids control may lead to an unnecessarily expensive drilling program and, in some instances, could even jeopardize the completion of drilling operations. Generally, there are two sources of solids in drilling fluids: (1) solids which are present from drilling fluid additives, or "solids-additives", and (2) solids present from the formation itself or "formation solids". It is important to accurately determine the amounts of solids, both from drilling fluid additives and the formation, in the drilling fluid. With accurate solids assessment, efficiency in a solids control circulation system can be achieved, and problems associated with drilling fluids can be diagnosed.

Two of the most common methods for determining the solids content of a drilling fluid sample are the retort analysis method and the cation exchange capacity (CEC) method. Both of these methods are well established in the art. Briefly, the retort analysis method determines total solids content in a drilling fluid by heating a fluid sample with known weight and volume to high temperatures to evaporate the liquid portions of the sample; what remains is the solids content. This test however does not provide information to separately determine the formation solids content and solids-additives content. See for example, American Petroleum Institute (API) Publication RP13B, pages 13-15, for a brief summary of the retort analysis method. The CEC method, on the other hand, correlates the number of exchangeable cations in the sample (cations in the sample that can be replaced by another cation, such as barium or ammonium) to the low gravity solids content. See for example, Van Olphen, H., "An Introduction to Clay Colloid Chemistry", Wiley-Interscience, New York, 1977, Chapter 5, and American Petroleum Institute Publication RP13B, "Recommended Practice for Standard Procedure in Testing Drilling Fluids", for a brief summary of CEC methods used in determining solids content in drilling fluid. The CEC method requires significant care in running the test and is not particularly suitable for wellsite use. In addition, the CEC does not provide a measurement of the formation solids and of the solids-additive, separately.

U.S. Ser. No. 175,081 to Kroeger et al. discloses a method for determining at wellsites the swelling-clay content of shales and shaly sandstone earth formations by dielectric measurements. Kroeger et al.'s method includes washing a sample of an earth formation with a fluid having a water activity substantially less than that of water to which a fluid cation may be added, measuring the sample's dielectric constant at a preselected frequency, and comparing the results of this measurement to calibration curves to obtain a measurement of the swelling-clay content of the formation. Kroeger et al.'s method describes different levels of determinations depending on the nature of the formation samples.

Currently, dielectric measurements are utilized for other, unrelated purposes. For example, dielectric measurements are utilized in logging tools for making determinations of the water and hydrocarbon content in sandstones and carbonates. These logging tools are not designed for making determinations of the solids content in drilling fluids. In addition, these logging tools lose their effectiveness in high-salinity fluids.

To the best of Applicants' knowledge, dielectric measurements are not used for making determinations of solids content in drilling fluids. In fact, excluding U.S. Ser. No. 175,081 to Kroeger et al., prior art actually dismisses dielectric responses observed between 1-50 MHz in dilute aqueous solids suspensions as anomalies which vanish with increasing salinity. See for example, Raythatha, R. and Sen, P. N., "Dielectric Properties of Clay Suspensions in the MHz to GHz Range", *Journal of colloid and Interface Science,* February 1986, Vol. 109, No. 2, in general, and particularly see pages 305 and 308 wherein it is stated that the electrochemical effects (of solids) become unimportant at high salinities and the geometrical effects dominate.

There exists a need for a rapid and reliable wellsite method for the determination of the solids content in drilling fluids. It is desirable to be able to obtain, at the wellsite, timely estimates of the total solids content of drilling fluids, including the portion corresponding to solids-additives and the portion corresponding to formation solids.

SUMMARY OF THE INVENTION

The present invention concerns a method for rapidly determining at the wellsite the solids content of drilling fluids. The invention describes a method for determining the solids content of drilling fluids by high-frequency dielectric measurements (for purposes of this application frequencies greater than 0.1 MHz are deemed "high frequency") which includes: collecting a drilling fluid sample that has been cleaned by the drilling fluid solids control system; cleaning the sample with a fluid which can dissolve residual oil and/or polymer bound on solids surfaces; separating the solids and liquid in the drilling fluid sample by means of centrifuging, thus creating a drilling fluid-solids sample and a drilling fluid-liquid sample; washing the drilling fluid-solids sample with a fluid having a water activity substantially less than that of water (using the dielectric constant as a measure of water activity, the dielectric constant of the fluid should be between 5 and 80) and which may contain a soluble cation (the soluble cations that may be added comprise: $Li^+$, $Na^+$, $K^+$, $Rb^+$, $Cs^+$, $(NH_4)^+$, $Mg^{+2}$, $Ca^{+2}$, $Ba^{+2}$, $Sr^{+2}$, $Co^{+2}$, $Ni^{+2}$, $Cu^{+2}$, $Zn^{+2}$, $La^{+3}$, $Fe^{+3}$, $Cr^{+3}$, $Al^{+3}$, or other similar cations); packing the washed drilling fluid-solids sample into a sample cell suitable for dielectric measurement; measuring the dielectric constant at a preselected frequency to allow uniform comparison of drilling fluid-solids samples (the frequency should be between 0.1 and 100 MHz); measuring the dielectric constant of drill cuttings in a manner similarly to the method used for the drilling fluid sample; measuring the dielectric constant of each solids-additive type that has been added to the drilling fluid, and obtaining the amount of formation solids present in the drilling fluid in accordance with the following relationship:

$$a = \frac{(DCM(ms) - X)}{(DCM(dc) - X)}$$

where:
a is amount of solids from the formation expressed as a fraction of total solids in the drilling fluid;
DCM(ms) is the dielectric constant of the drilling fluid-solids sample;
DCM(dc) is the dielectric constant of the drill cuttings sample;

$$X \text{ is } \sum_i^n b_i \, DCM(add_i)$$

is the weighted average of the dielectric constant for all solids-additive samples,
where:
DCM($add_i$) is the dielectric constant of solids-additive i; i=1 to n;
n is the number of solids-additive types; and
$b_i$ is the weight of solids-additive i as a fraction of the total solids-additive weight.

A determination of the solids content in drilling fluids may be performed at different levels depending on the information known about the drilling fluid being tested. Briefly, the method used in the determination of the solids content in drilling fluids varies depending on whether the quantities of solids-additives in the drilling fluid are known. Also, the method used in the determination of solids content varies depending on the nature of the drilling fluid. Briefly, drilling fluids may be classified in three broad categories: water-base drilling fluids, oil-base drilling fluids, and water-base polymer drilling fluids. Depending on which class of drilling fluid is tested, a different initial cleaning procedure is used. The different cleaning procedures are described in more detail in the detailed description of the invention which follows.

It is an advantage of this invention that it can quantify at wellsites in a timely manner the formation solids present in drilling fluids.

It is also an advantage of this invention that it can determine at wellsites in a timely manner the quantities of solids-additive types added to the drilling fluid, if these quantities are unknown, in addition to determining the amounts of formation solids present in the drilling fluid, and the overall solids content of the drilling fluid.

DETAILED DESCRIPTION OF THE PREFERRED EMBODIMENT

Figure 1:
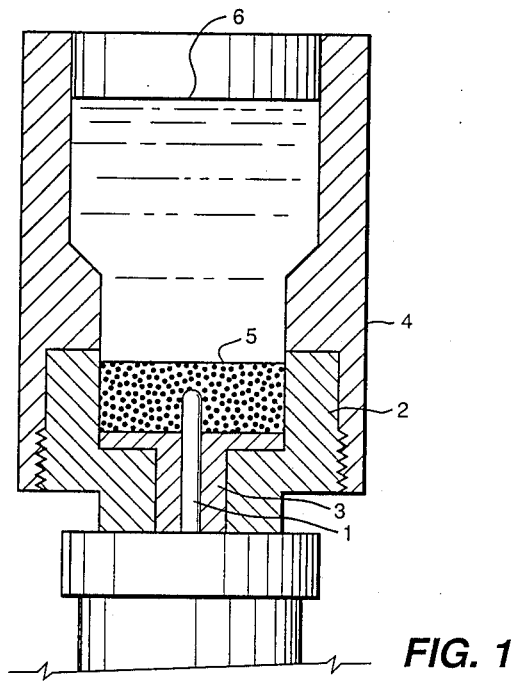
FIG. 1 schematically illustrates a sample cell suitable for dielectric constant measurements.

The present invention concerns a timely wellsite method for determining the solids content of drilling fluids. The principal steps in the preferred embodiment of this method include: cleaning a drilling fluid sample with a fluid having a water activity substantially less than that of water; separating the solids and liquid in the drilling fluid sample by means of centrifuging, thus creating a drilling fluid-solids sample and a mud-liquid sample; washing the drilling fluid-solids sample with a fluid having a water activity substantially less than that of water to which a cation has been added; packing the washed drilling fluid-solids sample into a sample cell suitable for dielectric measurement; measuring the dielectric constant of the washed drilling fluid-solids sample at a preselected frequency; grinding a sample of drill cuttings from the same formation to a size suitable for testing; washing and packing the drill cuttings sample into a sample cell suitable for dielectric measurement; measuring the dielectric constant of the drill cuttings sample at the same preselected frequency used for measuring the dielectric constant of the drilling fluid-solids sample; grinding a sample of each solids-additive type which has been added to the drilling fluid to sizes suitable for testing; washing, packing, and measuring the dielectric constant of each of the solids-additive samples at the same preselected frequency used for measuring the dielectric constant of the drilling fluid-solids sample and the drill cuttings sample; obtaining the amount of formation solids present in the drilling fluid in accordance with the following relationship:

$$a = \frac{(DCM(ms) - X)}{(DCM(dc) - X)} \qquad (1)$$

where:
a is amount of solids from the formation expressed as a fraction of total solids in the drilling fluid;
DCM(ms) is the dielectric constant of the drilling fluid-solids sample;
DCM(dc) is the dielectric constant of the drilling cuttings-sample;

$$X \text{ is } \sum_i^n b_i DCM(add_i)$$

which is the weighted average of the dielectric constant for all solids-additive types added to the drilling fluid;
DCM($add_i$) is the dielectric constant of solids-additive i, i=1 to n;
n is the number of solids-additive types; and
$b_i$ is the weight of solids-additive i as a fraction of the total solids-additive weight.

The invention will now be described in greater detail with reference to the accompanying drawings.

In the preferred embodiment of the invention, two levels of solids determination are possible. These levels of determination depend upon whether the quantities of solids-additive added to the drilling fluid are known.

The first level of determination is suitable for determining the content of formation solids present in drilling fluids which have known types and quantities of solids-additives.

The second level of determination is suitable for determining the content of formation solids present in drilling fluids which have known types of solids-additives but which have unknown quantities of each such solids-additives types. Thus, the second level of determination provides the solids content of formation solids plus the solids content of each solids-additive type present in the drilling fluid.

In each of the two levels of determination, the initial cleaning procedures for the drilling fluid samples differ depending on the type of drilling fluid tested. Thus, the cleaning procedure used for an oil-base drilling fluid differs from the cleaning procedure used for a water-base drilling fluid, and from the procedure used for a water-base polymer fluid.

The two different levels of determination will now be described in greater detail.

As mentioned earlier, the first level of determination requires that the types of solids added to the drilling fluid or "solids-additives types" be known, as well as the quantities of these solids-additives types that have been added to the drilling fluid.

The following description is based on the method used for oil-base drilling fluids.

A drilling fluid sample is collected after it has been cleaned through the drilling fluids solids control equipment in the circulation system of a drilling complex. In a typical measuring routine, a volume of ½ cubic centimeter of drilling fluid is placed in an 8 milliliter test tube. The test tube is nearly filled with an organic solvent such as acetone to dissolve the oil, emulsifier, and/or other organic substances present in the drilling fluid. The drilling fluid sample and organic solvent are then agitated or "vortexed" to provide satisfactory mixing of the drilling fluid and the organic solvent. The test tube is then allowed to sit for a period suitable for the organic solvent to dissolve the oil, emulsifier, and/or other organic substances. This period of time may vary with experimental technique, but it is usually short, about one or two minutes. The drilling fluid sample is then centrifuged to separate the solids and liquid, and the liquid is decanted, and discarded. The drilling fluid-solids sample remaining is then washed with a solvent miscible in both water and the organic solvent and again centrifuged to separate out the organic solvent and the drilling fluid-solids sample. The drilling fluid-solids sample is then washed with a fluid having a water activity substantially less than that of water to which a cation may be added, such as sodium chloride (if sodium chloride is used, a preferred concentration is 37.7 grams of sodium chloride per liter of sample). Sodium cations are exchanged with all exchangeable cations in the sample and place all swelling solids, such as swelling clays, in their most swellable states. Naturally occurring swelling clays, such as mortmorillonite, smectite, or bentonite may contain either sodium, calcium, potassium, or magnesium as exchangeable cations, or any combination of the four. This example utilizes sodium as the exchangeable cation. However, it is emphasized that other cations may be utilized in place of sodium to standardize the interlayer cations. Such other cations are: $Li^+$, $K^+$, $Rb^+$, $Cs^+$, $(NH_4)^+$, $Ca^{+2}$, $Ba^{+2}$, $Sr^{+2}$, $Co^{+2}$, $Ni^{+2}$, $Cu^{+2}$, $Zn^{+2}$, $La^{+3}$, $Fe^{+3}$, $Cr^{+3}$, $Al^{+3}$. For this level of determination non-swelling state cations as well as swelling-state cations may be utilized.

Using the dielectric constant as a measure of water activity, the fluid's dielectric constant should range between about 5 and 80. This fluid attenuates the swelling behavior of solids such that it will permit subsequent sample treatment and measurement. A fluid suitable for this purpose is an alcohol-water mixture. A suitable alcohol-water mixture which is commonly available is rubbing alcohol (70% isopropyl alcohol and 30% water by volume). The dielectric constant of this alcohol-water mixture is about 35, which corresponds to a suitable water activity level.

Samples which have been washed with cation-containing fluids, for example sodium chloride, lanthanum chloride, or potassium chloride, are then washed with the non-cation-containing fluid, such as the rubbing alcohol, until the conductivity of the decantate is no more than twice that of the washing fluid in its original state (without the addition of salts). This level of conductivity represents the effective removal of excess exchanged cations from the washing fluid.

Subsequent to the washing step, the sample is packed into a sample cell suitable for dielectric constant measurements, such as the sample cell illustrated in FIG. 1. The use of coaxial sample cells for dielectric measurements at frequencies above 0.1 MHz are well established in the art. The coaxial design for the sample cell is used because of the ease of adding the slurry to the cell and because of the ease of packing the sample into the cell around the inner coaxial conductor by centrifuge methods. As shown in FIG. 1, a suitable sample cell is of a coaxial geometry, consisting of a center conductor 1 and an outer conductor 2 separated by a teflon spacer 3. A plastic jacket 4 has been attached to the outer conductor 2. The sample 5 and fluid 6 are added to the cavity of the sample cell. When the sample 5 has been packed into the sample cell, the sample 5 resides between the center conductor 1 and outer conductor 2, above the teflon spacer 3, and completely covers the center conductor 1. The fluid 6 is contained above the sample 5 and is contained within the plastic jacket 4.

In order to transfer the washed sample to this sample cell, portions of the non-cation-containing fluid are added to the sample. The sample and fluid are vortexed to provide satisfactory mixing, and the slurry is transferred into the sample cell.

The slurry-filled sample cell is then centrifuged to pack the sample into the sample cell. For example, centrifuging the sample at a rate of 1800 revolutions per minute for one minute uniformly packs the sample between the inner and outer conductors of the coaxial sample cell leaving the fluid in the plastic jacket above the measuring portion of the sample cell. This centrifuging rate is suggested because it is a moderate rate for small, portable centrifuges and because the rate and duration are sufficient to adequately pack the solids into the sample cell.

The sample cell is then attached to a capacitance meter operating at a set frequency. Capacitance meters are well known in the art and are commonly available. A suitable test frequency is 1 MHz. A frequency of 1 MHz is sufficiently high to avoid electrode-polarization effects which distort measurements at lower frequencies and is sufficiently low to quantify the magnitude of the swelling-clay dielectric response. This dielectric response originates within the interlayer region of the swelling clay. This response occurs due to the reduced mobility of the interlayer exchangeable cations (for example, $Na^+$ or $La^{+3}$).

The sample's capacitance is measured and converted to the dielectric constant by well established methods.

Briefly, the capacitances of two standards placed in the cell may be measured (for example, air whose dielectric constant is 1 and distilled water whose dielectric constant is 78 at a temperature of 25° C). A linear relationship may then be established between the measured capacitance and the dielectric constant.

The dielectric constant of the samples is measured at 1 MHz. The duration of entire measurement process, including washing and sodium cation exchange, takes about 3 hours. The amount of solids (from the formation) is determined in accordance with the following relationship:

$$a = \frac{(DCM(ms) - X)}{(DCM(dc) - X)} \quad (1)$$

where:
a is amount of solids from the formation expressed as a fraction of total solids in the drilling fluid;
DCM(ms) is the dielectric constant of the drilling fluid-solids sample;
DCM(dc) is the dielectric constant of the drill cuttings sample;

$$X \text{ is } \sum_{i}^{n} b_i DCM(add_i)$$

is the weighted average of the dielectric constant for all solids-additive samples,
where:
$DCM(add_i)$ is the dielectric constant of solids-additive i, i=1 to n;
n is the number of solids-additive types; and
$b_i$ is the weight of solids-additive i as a fraction of the total solids-additive weight.

An experiment was conducted to validate the described method. An oil mud was formulated with the additives listed in Table 1. Then different amounts of solids were added in the mud to form different mud samples (F to M). Barite was added to increase the mud weight. Kaolinite was used to simulate inert formation solids, and Panther Creek clay, which contains mostly smectite, was used to simulate active formation solids. The dielectric constants of all the solids-additives and drill cuttings used in this experiment were measured and listed in Table 2. Among the solids added in the oil mud, only Panther Creek clay had a high dielectric constant of approximately 200. Geltone is a smectite clay treated with organic material to make it organophilic or oil wetting and nonhyrating; therefore, its dielectric constant is low. Duratone is an organophilic lignite with a low dielectric constant. These products remain stable even when they were washed by acetone.

Figure 2:
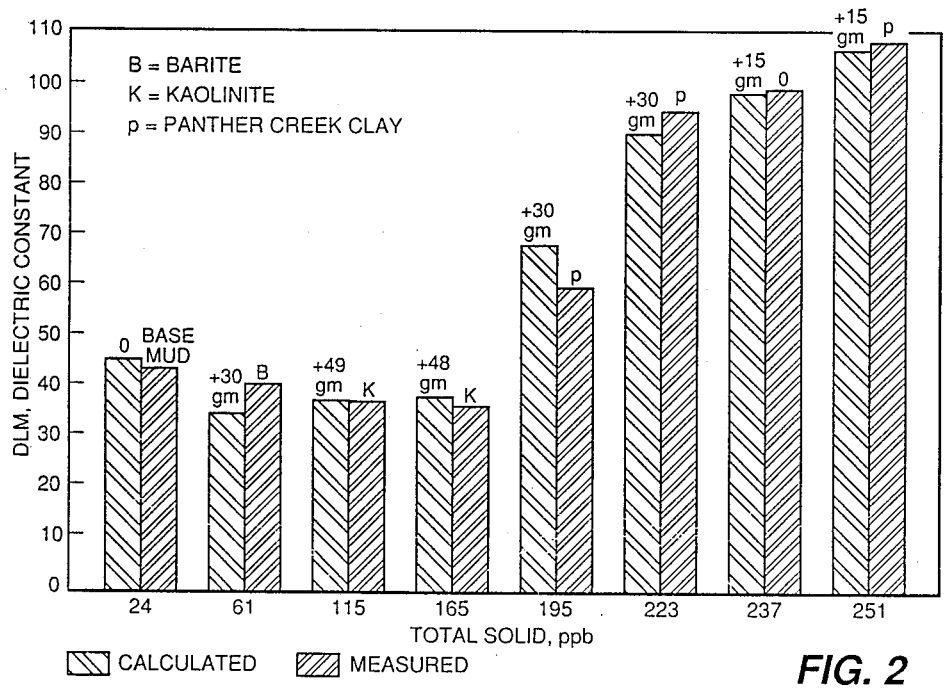
FIG. 2 is a comparison of the measured and calculated dielectric constants for different types of drilling fluid samples versus the total solids content of each such sample.

A total of seven oil mud samples were formulated for this experiment. Table 3 listed the amount of solids in each mud sample. The dielectric constant for each mud sample was measured using the procedures described above. In these tables DCM means dielectric constant measurement. The dielectric constant was also calculated using Equation 1. It was observed that the dielectric constant increased with increasing amount of solids (Panther Creek clay) in the drilling fluid. It was also found that the calculated dielectric constants for all mud samples were in good agreement with the measured values (see Table 4C). FIG. 2 illustrates the comparison of the calculated values with the measurements. The good agreement between the measured and calculated values shows that the dielectric method is a reliable technique to measure the solids content in drilling fluids.

TABLE 1

| Oil Mud Formation - 1 bbl Equivalent | |
|---|---|
| Additives | Amount |
| Mentor 26 oil | 230.6 cc |
| Invermul | 8 gm |
| Lime | 6 gm |
| Duratone HT | 10 gm |
| Geltone II | 5 gm |
| Water | 57.75 cc |
| CaCl₂ | 29.1 gm |
| EZ Mul | 2 gm |

TABLE 2

| Properties of the Oil Mud Solids | |
|---|---|
| Additives | DCM |
| Lime | 30 |
| Duratone | 48 |
| Geltone | 53 |
| Barite | 28 |
| Kaolinite | 40 |
| Panther Creek clay | 200 |

TABLE 3

| Solids Content of Oil Mud Samples | |
|---|---|
| Sample (ID) | Mud Solids |
| F | Base Mud - See Table 1 |
| G | F + 31.4 gm Barite |
| H | G + 48.7 gm Kaolinite |
| I | H + 48.0 gm Kaolinite |
| J | I + 30.0 gm Panther Creek clay |
| K | J + 30.0 gm Panther Creek clay |
| L | K + 15.0 gm Panther Creek clay |
| M | L + 15.0 gm Panther Creek clay |

TABLE 4A

DCM Calculation for Mud Formulated in the Laboratory
DRILLING FLUID TYPE: Oil-Base Drilling Fluid

| Solids-Additive Types | Amount, gm | % Weight | DCM-Pure Additive | Weighted DCM |
|---|---|---|---|---|
| Lime | 6 | 20 | 30 | 8.80 |
| Duratone | 10 | 48 | 48 | 22.86 |
| Geltone | 5 | 24 | 53 | 12.62 |

Total Solids = 21 gm
Calculated DCM = 44.28
Measured DCM = 42.85

TABLE 4B

DCM Calculation for Mud Formulated in the Laboratory
DRILLING FLUID WITH DIFFERENT SOLIDS: DCM Calculation

| ID | Solids Types | Amount gm | DCM Pure Solids | Mud Volume, CC | | | Solid Weight, gm | | Solids Content lb/bbl |
|---|---|---|---|---|---|---|---|---|---|
| | | | | Initial | Addition Solids | Total | Addition Solids | Total | |
| F | BASE | .0 | 44 | 310 | .0 | 310 | 21.0 | 21.0 | 24 |
| G | BAR* | 31.5 | 28 | 290 | 7.5 | 297 | 19.6 | 51.2 | 60 |
| H | KAO* | 48.7 | 40 | 281 | 16.0 | 296 | 48.3 | 97.0 | 114 |
| I | KAO | 48.0 | 40 | 282 | 16.0 | 297 | 92.1 | 140.0 | 165 |

TABLE 4B-continued

DCM Calculation for Mud Formulated in the Laboratory
DRILLING FLUID WITH DIFFERENT SOLIDS: DCM Calculation

| ID | Solids Types | Amount gm | DCM Pure Solids | Mud Volume, CC | | | Solid Weight, gm | | Solids Content lb/bbl |
|----|----|----|----|----|----|----|----|----|----|
| | | | | Initial | Addition Solids | Total | Addition Solids | Total | |
| J | SMEC* | 30.0 | 200 | 283 | 11.0 | 294 | 133.0 | 163.0 | 194 |
| K | SMEC | 30.0 | 200 | 279 | 11.0 | 290 | 154.7 | 184.7 | 222 |
| L | SMEC | 30.0 | 200 | 277 | 11.0 | 288 | 175.8 | 205.8 | 250 |
| M | SMEC | | | AVERAGE OF MUD K AND L | | | | | 234 |

*BAR = Barite
*KAO = Kaolinite to simulate inert formation solids
*SMEC = Panther Creek Smectite clay to simulate active formation solids

TABLE 4C

DCM Calculation for Mud Formulated in the Laboratory
DRILLING FLUID WITH DIFFERENT SOLIDS:
Dielectric Constant Measurement (DCM) Comparison

| ID | DCM Calculated | Measured | Calculated/Measured |
|----|----|----|----|
| F | 44.3 | 42.9 | 1.03 |
| G | 34.2 | 39.9 | 0.85 |
| H | 37.1 | 36.9 | 1.00 |
| I | 38.1 | 35.9 | 1.06 |
| J | 67.9 | 59.4 | 1.14 |
| K | 89.4 | 94.4 | 0.94 |
| L | 105.5 | 108.2 | 0.97 |
| M | 97.2 | 98.7 | 0.98 |
| AVERAGE RATIO OF CALCULATED DCM/MEASURED DCM | | | 1.00 |

The second level of determination is required when unknown amounts of solids-additives have been added to the drilling fluid. In this case the amount of solids from the formation, as well as, solids-additives added during the drilling operation are unknown.

By way of illustration, a description of the level two determination is presented below for an oil-base drilling fluid, where the types of solids-additives are known, but quantities of said solids-additives are unknown.

A drilling fluid sample is first cleaned with an organic solvent (such as an xylene based solvent, acetone, or toluene) having a water activity substantially less than that of water; the solids and liquid in the drilling fluid sample are then separated by means of centrifuging, thus creating a drilling fluid-solids sample and a drilling fluid-liquid sample, the drilling fluid-liquid sample is decanted and discarded; the drilling fluid-solids sample is then cleaned again with a solvent (such as acetone) miscible in both water and the organic solvent, and washed with a fluid having a water activity substantially less than that of water to which a cation has been added; the washed drilling fluid-solids sample is then packed into a sample cell suitable for dielectric measurement; and the dielectric constant of the washed drilling fluid-solids sample is measured at a preselected frequency; a sample of drill cuttings from the same formation is ground to a size suitable for testing, and the washing and the packing steps are repeated for the drill cuttings sample; the dielectric constant of the drill cuttings sample is measured at the same preselected frequency used for the drilling fluid-solids sample; for each solids-additive type which has been added to the drilling fluid, n+1 samples of each such solids-additive types are ground to sizes suitable for testing (where n is the number of types of solids-additives added to the drilling fluid); and each such solids-additive sample is then washed with a fluid having a water activity substantially less than that of water to which a cation has been added (whereby a different type of cation is used for each such n+1 samples of solids-additive type, thus resulting in n+1 washings for each of the n types of solids-additives added to the drilling fluid); the washing and the packing steps are repeated for each such solids-additive type; and the dielectric constant of each of the n+1 solids-additive samples is then measured for each of the solids-additive type added to the drilling fluid at the same preselected frequency used in the previous dielectric constant measurements; the amount of formation solids present in the oil-base drilling fluid sample and the quantities of each solids-additive type added to the drilling fluid are then obtained in accordance with the following relationship:

$$DCM(ms)_j = aDCM(dc)_j + \sum_i^n b_i DCM(add_i)_j$$

where:
a is amount of solids from the formation expressed as a fraction of total solids in the drilling fluid;
DCM(ms) is the dielectric constant of the drilling fluid-solids sample;
DCM(dc) is the dielectric constant of the drill cuttings sample;
j is the type of cation used;
$DCM(add_i)$ is the dielectric constant of solids-additive i, i=1 to n;
n is the number of solids-additive types; and
$b_i$ is the weight factor of solids-additive type i as a fraction of the total solids weight.

This will result in a total of m=n+1 equations and m=n+1 unknowns which can be resolved mathematically to obtain the amount of formation solids present in the oil-base drilling fluid sample and the quantitities of each solids-additive type added to the drilling fluid.

The determination of the solids content, including a determination of the quantity of solids present for each additive type added to the drilling fluid as well as the solids from the formation carried away by the action of the drilling fluid during operation may be obtained by solving the resulting set of homogeneous linear equations which are obtained as described above.

For example, in a drilling fluid system in which three different types of solids-additive types have been added to the drilling fluid in unknown quantities, a set of homogeneous linear equations may be obtained, one for each washing with a different type of cation. For purposes of illustration, the cations used in this example are: $Na^+$, $K^+$, $Li^+$, and $Cs^+$. The resulting linear equations would be in the form:

DCM(ms)$_{Na}$=a
  DCM(dc)$_{Na}$+b$_1$DCM(add$_1$)$_{Na}$+b$_i$DCM(add$_2$)$_{Na}$ b$_3$ DCM(add$_3$)$_{Na}$ DCM(ms)$_K$=a DCM(dc)$_K$+b$_1$DCM(add$_1$)$_K$+b$_2$ DCM(add$_2$)$_K$+b$_3$ DCM(add$_3$)$_K$ DCM(ms)$_{Li}$=a
  DCM(dc)$_{Li}$+b$_1$DCM(add$_1$)$_{Li}$+b$_2$DCM(add$_2$)$_{Li}$+b$_3$ DCM(add$_3$)$_{Li}$ DCM(ms)$_{Cs}$=a
  DCM(dc)$_{Cs}$+b$_1$DCM(add$_1$)$_{Cs}$+b$_2$DCM(add$_2$)$_{Cs}$+b$_3$ DCM(add$_3$)$_{Cs}$ or expressed in a different form:

$$1 = \frac{aDCM(dc)_{Na}}{DCM(ms)_{Na}} + \frac{b_1DCM(add_1)_{Na}}{DCM(ms)_{Na}} + \frac{b_2DCM(add_2)_{Na}}{DCM(ms)_{Na}} + \frac{b_3DCM(add_3)_{Na}}{DCM(ms)_{Na}};$$

$$1 = \frac{aDCM(dc)_K}{DCM(ms)_K} + \frac{b_1DCM(add_1)_K}{DCM(ms)_K} + \frac{b_2DCM(add_2)_K}{DCM(ms)_K} + \frac{b_3DCM(add_3)_K}{DCM(ms)_K};$$

$$1 = \frac{aDCM(dc)_{Li}}{DCM(ms)_{Li}} + \frac{b_1DCM(add_1)_{Li}}{DCM(ms)_{Li}} + \frac{b_2DCM(add_2)_{Li}}{DCM(ms)_{Li}} + \frac{b_3DCM(add_3)_{Li}}{DCM(ms)_{Li}};$$

and $$1 = \frac{aDCM(dc)_{Cs}}{DCM(ms)_{Cs}} + \frac{b_1DCM(add_1)_{Cs}}{DCM(ms)_{Cs}} + \frac{b_2DCM(add_2)_{Cs}}{DCM(ms)_{Cs}} + \frac{b_3DCM(add_3)_{Cs}}{DCM(ms)_{Cs}}$$

The above system of homogeneous linear equation define a matrix of coefficients in the following form:

$$[C] \times [B] = [1],$$

where:

$$[C] = \begin{bmatrix} \frac{DCM(dc)_{Na}}{DCM(ms)_{Na}} & \frac{DCM(add_1)_{Na}}{DCM(ms)_{Na}} & \frac{DCM(add_2)_{Na}}{DCM(ms)_{Na}} & \frac{DCM(add_3)_{Na}}{DCM(ms)_{Na}} \\ \frac{DCM(dc)_K}{DCM(ms)_K} & \frac{DCM(add_1)_K}{DCM(ms)_K} & \frac{DCM(add_2)_K}{DCM(ms)_K} & \frac{DCM(add_3)_K}{DCM(ms)_K} \\ \frac{DCM(dc)_{Li}}{DCM(ms)_{Li}} & \frac{DCM(add_1)_{Li}}{DCM(ms)_{Li}} & \frac{DCM(add_2)_{Li}}{DCM(ms)_{Li}} & \frac{DCM(add_3)_{Li}}{DCM(ms)_{Li}} \\ \frac{DCM(dc)_{Cs}}{DCM(ms)_{Cs}} & \frac{DCM(add_1)_{Cs}}{DCM(ms)_{Cs}} & \frac{DCM(add_2)_{Cs}}{DCM(ms)_{Cs}} & \frac{DCM(add_3)_{Cs}}{DCM(ms)_{Cs}} \end{bmatrix}$$

and $$[B] = \begin{bmatrix} a \\ b_1 \\ b_2 \\ b_3 \end{bmatrix}$$

The matrix's solution provides the solids content of the drilling fluid, including the content of formation solids and the content of solids-additives added to the drilling fluid, as well as the content of the solids for each solids-additives type added. That is, it provides a solution to coefficients a, b$_1$, b$_2$, and b$_3$.

As mentioned earlier the initial cleaning procedures for the drilling fluid depend on the nature of the drilling fluid. That is, whether the drilling fluid is a water-base drilling fluid, an oil-base drilling fluid, or a water-base polymer drilling fluid.

The following different types of fluids are considered suitable for each of the three different drilling fluid types. For oil-base drilling fluids an organic solvent such as acetone or a xylene-based solvent are considered suitable. For a water-base, clay drilling fluid, an alcohol-water mixture such as rubbing alcohol (70% isopropyl alcohol and 30% water) is considered suitable, and for water-base polymer drilling, an acid and/or an alcohol-water mixture is suitable.

The above description and examples of the invention are offered only for the purpose of illustration, and it is not intended that the invention be limited except by the scope of the appended claims.

We claim:

1. A method for determining the content of formation solids present in drilling fluids by dielectric measurements, comprising the steps of:
   (a) cleaning a drilling fluid sample with a fluid having a water activity substantially less than that of water;
   (b) separating the solids and liquid in the drilling fluid sample by means of centrifuging, thus creating a drilling fluid-solids sample and a drilling fluid-liquid sample;
   (c) washing the drilling fluid-solids sample with a fluid having a water activity substantially less than that of water to which a cation has been added;
   (d) packing the washed drilling fluid-solids sample into a sample cell suitable for dielectric measurement;
   (e) measuring the dielectric constant of the washed drilling fluid-solids sample at a preselected frequency;
   (f) grinding a sample of drill cuttings from the same formation to a size suitable for testing;
   (g) repeating the washing step (c) and the packing step (d) for the drill cuttings sample;
   (h) measuring the dielectric constant of the drill cuttings sample at the same preselected frequency used in step (e);

(i) for each solids-additive type which has been added to the drilling fluid, grinding a sample of each such solids-additive type to sizes suitable for testing;

(j) repeating the washing step (c) and the packing step (d) for each such solids-additive type samples;

(k) measuring the dielectric constant of each of the solids-additive samples at the same preselected frequency used in steps (e) and (h);

(l) obtaining the amount of formation solids present in the drilling fluid sample in accordance with the following relationship:

$$a = \frac{(DCM(ms) - X)}{(DCM(dc) - X)}$$

where:

a is amount of solids from the formation expressed as a fraction of total solids in the drilling fluid;

DCM(ms) is the dielectric constant of the drilling fluid-solids sample obtained in step (e);

DCM(dc) is the dielectric constant of the drilling cuttings sample obtained in step (h);

$$X \text{ is } \sum_i^n b_i \, DCM(add_i)$$

is the weighted average of the dielectric constant for all solids-additive samples obtained in step (k), where DCM(add$_i$) is the dielectric constant of solids-additive type i, i=1 to n;

n is the number of solids-additive types; and b$_i$ is the weight factor of of solids-additive i as a fraction of the total solids weight.

2. A method for determining the content of formation solids present in oil-base drilling fluids, with known types and quantities of solids-additives, by dielectric measurements, comprising the steps of:

(a) cleaning a drilling fluid sample with an organic solvent having a water activity substantially less than that of water;

(b) separating the solids and liquid in the drilling fluid sample by means of centrifuging, thus creating a drilling fluid-solids sample and a drilling fluid-liquid sample;

(c) washing the drilling fluid-solids sample with a solvent miscible in both water and the organic solvent and centrifuging said sample to separate out the organic solvent;

(d) washing the drilling fluid-solids sample with a fluid having a water activity substantially less than that of water to which a cation has been added and centrifuging said sample to separate out said fluid;

(e) packing the washed drilling fluid-solids sample into a sample cell suitable for dielectric measurement;

(f) measuring the dielectric constant of the washed drilling fluid-solids sample at a preselected frequency;

(g) grinding a sample of drill cuttings from the formation to a size suitable for testing;

(h) repeating the washing step (d) and the packing step (e), for the drill cuttings sample;

(i) measuring the dielectric constant of the drill cuttings sample at the same preselected frequency used in step (f);

(j) for each solids-additive type which has been added to the drilling fluid, grinding a sample of each such solids-additive type to sizes suitable for testing;

(k) repeating the washing step (d) and packing step (e) for each such solids-additive sample;

(l) measuring the dielectric constant of each of the solids-additive samples at the same preselected frequency used in steps (f) and (i);

(m) obtaining the amount of formation solids present in the oil-base drilling fluid sample in accordance with the following relationship:

$$a = \frac{(DCM(ms) - X)}{(DCM(dc) - X)}$$

where:

a is amount of solids from the formation expressed as a fraction of total solids in the drilling fluid;

DCM(ms) is the dielectric constant of the drilling fluid-solids sample obtained in step (f);

DCM(dc) is the dielectric constant of the drilling cuttings sample obtained in step (i);

$$X \text{ is } \sum_i^n b_i \, DCM(add_i)$$

is the weighted average of the dielectric constant for all solids-additive samples obtained in step (l), where:

DCM(add$_i$) is the dielectric constant of solids-additive i, i=1 to n;

n is the number of solids-additive types; and b$_i$ is the weight factor of of solids-additive i as a fraction of the total solids weight.

3. A method for determining the content of formation solids present in water-base drilling fluids, with known types and quantities of solids-additives, by dielectric measurements, comprising the steps of:

(a) cleaning a drilling fluid sample with a fluid having a water activity substantially less than that of water;

(b) separating the solids and liquid in the drilling fluid sample by means of centrifuging, thus creating a drilling fluid-solids sample and a drilling fluid-liquid sample;

(c) washing the drilling fluid-solids sample with a fluid having a water activity substantially less than that of water to which a cation has been added;

(d) packing the washed drilling fluid-solids sample into a sample cell suitable for dielectric measurement;

(e) measuring the dielectric constant of the washed drilling fluid-solids sample at a preselected frequency;

(f) grinding a sample of drill cuttings from the same formation to a size suitable for testing;

(g) repeating the washing step (c) and the packing step (d), for the drill cuttings sample;

(h) measuring the dielectric constant of the drill cuttings sample at the same preselected frequency used in step (e);

(i) for each solids-additive type which has been added to the drilling fluid, grinding a sample of each such solids-additive type to sizes suitable for testing;

(j) repeating steps (c) and (d) for each such solids-additive type sample;

(k) measuring the dielectric constant of each of the solids-additive samples at the same preselected frequency used in steps (e) and (h);

(l) obtaining the amount of formation solids present in the drilling fluid sample in accordance with the following relationship:

$$a = \frac{(DCM(ms) - X)}{(DCM(dc) - X)}$$

where
- a is amount of solids from the formation expressed as a fraction of total solids in the drilling fluid;
- DCM(ms) is the dielectric constant of the drilling fluid-solids sample obtained in step (e);
- DCM(dc) is the dielectric constant of the drill cuttings sample obtained in step (h);

$$X \text{ is } \sum_{i}^{n} b_i \, DCM(add_i)$$

is the weighted average of the dielectric constant for all solids-additive samples obtained in step (k);

where:
- $DCM(add_i)$ is the dielectric constant of solids-additive i, i=1 to n;
- n is the number of solids-additive types; and
- $b_i$ is the weight factor of solids-additive i as a fraction of the total solids weight.

4. A method for determining the content of formation solids present in water-base polymer drilling fluids, with known types and quantities of solids-additives, by dielectric measurements, comprising the steps of:

(a) cleaning a drilling fluid sample with a fluid having a pH in the acid range;

(b) separating the solids and liquid in the drilling fluid sample by means of centrifuging, thus creating a drilling fluid-solids sample and a drilling fluid-liquid sample;

(c) washing the drilling fluid-solids sample with a fluid having a water activity substantially less than that of water to which a cation has been added;

(d) packing the washed drilling fluid-solids sample into a sample cell suitable for dielectric measurement;

(e) measuring the dielectric constant of the washed drilling fluid-solids sample at a preselected frequency;

(f) grinding a sample of drill cuttings from the same formation to a size suitable for testing;

(g) repeating the washing step (c) and the packing step (d), for the drill cuttings sample;

(h) measuring the dielectric constant of the drill cuttings sample at the same preselected frequency used in step (e);

(i) for each solids-additive type which has been added to the drilling fluid, grinding a sample of each such solids-additive type to sizes suitable for testing;

(j) repeating the washing step (c) and the packing step (d) for each such solids-additive sample;

(k) measuring the dielectric constant of each of the solids-additive samples at the same preselected frequency used in steps (e) and (h);

(l) obtaining the amount of formation solids present in the drilling fluid sample in accordance with the following relationship:

$$a = \frac{(DCM(ms) - X)}{(DCM(dc) - X)}$$

where:
- a is amount of solids from the formation expressed as a fraction of total solids in the drilling fluid;
- DCM(ms) is the dielectric constant of the drilling fluid-solids sample obtained in step (e);
- DCM(dc) is the dielectric constant of the drilling cuttings sample obtained in step (h);

$$X \text{ is } \sum_{i}^{n} b_i \, DCM(add_i)$$

is the weighted average of the dielectric constant for all solids-additive samples obtained in step (k),
- $DCM(add_i)$ is the dielectric constant of solids-additive i, i=1 to n;
- n is the number of solids-additive types; and
- $b_i$ is the weight factor of solids-additive i as a fraction of the total solids weight.

5. A method for determining the content of formation solids present in oil-base drilling fluids, with known types of solids-additives but unknown quantities of said solids-additives, by dielectric measurements, comprising the steps of:

(a) cleaning a drilling fluid sample with an organic solvent having a water activity substantially less than that of water;

(b) separating the solids and liquid in the drilling fluid sample by means of centrifuging, thus creating a drilling fluid-solids sample and a drilling fluid-liquid sample;

(c) washing the drilling fluid-solids sample with a solvent miscible in both water and the organic solvent;

(d) washing the drilling fluid-solids sample with a fluid having a water activity substantially less than that of water to which a cation has been added;

(e) packing the washed drilling fluid-solids sample into a sample cell suitable for dielectric measurement;

(f) measuring the dielectric constant of the washed drilling fluid-solids sample at a preselected frequency;

(g) grinding a sample of drill cuttings from the same formation to a size suitable for testing;

(h) repeating the washing step (d) and the packing step (e), for the drill cuttings sample;

(i) measuring the dielectric constant of the drill cuttings sample at the same preselected frequency used in step (f);

(j) for each solids-additive type which has been added to the drilling fluid, grinding n+1 samples of each such solids-additive type to sizes suitable for testing, where n is the number of types of solids-additives added to the drilling fluid;

(k) for each solids-additive sample obtained in step (j), washing each such solids-additive sample with a fluid having a water activity substantially less than that of water to which a cation has been added, whereby a different type of cation is used for each such n+1 samples of solids-additive type, thus resulting in n+1 washings for each of the n types of solids-additives added to the drilling fluid;

(l) repeating the washing step (d) and the packing step (e) for each such solids-additive type;

(m) measuring the dielectric constant of each of the n+1 solids-additive samples for each of the solids-additive types added to the drilling fluid at the same preselected frequency used in steps (f) and (i);

(n) obtaining the amount of formation solids present in the oil-base drilling fluid sample and the quantities of each solids-additive type added to the drilling fluid in accordance with the following relationship, which will result in a total of m=n+1 equations and m=n+1 unknowns which can be resolved mathematically to obtain the amount of formation solids present in the oil-base drilling fluid sample and the quantitities of each solids-additive type added to the drilling fluid:

$$DCM(ms)_j = aDCM(dc)_j + \sum_{i}^{n} b_i DCM(add_i)_j$$

where:
a is amount of solids from the formation expressed as a fraction of total solids in the drilling fluid;
DCM(ms) is the dielectric constant of the drilling fluid-solids sample obtained in step (f);
DCM(dc) is the dielectric constant of the drill cuttings sample obtained in step (i);
j is the type of cation used in step k;
$DCM(add_i)$ is the dielectric constant of solids additive i, i=1 to n;
n is the number of solids-additive types; and
$b_i$ is the weight factor of solids-additive type i as a fraction of the total solids weight.

6. A method for determining the content of formation solids present in water-base clay drilling fluids, with known types of solids-additives but unknown quantities of said solids-additives, by dielectric measurements, comprising the steps of:

(a) cleaning a drilling fluid sample with a fluid having a water activity substantially less than that of water;

(b) separating the solids and liquid in the drilling fluid sample by means of centrifuging, thus creating a drilling fluid-solids sample and a drilling fluid-liquid sample;

(c) washing the drilling fluid-solids sample with fluid having a water activity substantially less than that of water to which a cation has been added;

(d) packing the washed drilling fluid-solids sample into a sample cell suitable for dielectric measurement;

(e) measuring the dielectric constant of the washed drilling fluid-solids sample at a preselected frequency;

(f) grinding a sample of drill cuttings from the same formation to a size suitable for testing;

(g) repeating the washing step (c) and the packing step (d), for the drill cuttings sample;

(h) measuring the dielectric constant of the drill cuttings sample at the same preselected frequency used in step (e);

(i) for each solids-additive type which has been added to the drilling fluid, grinding n+1 samples of each such solids-additive type to sizes suitable for testing where n is the number of types of solids-additives added to the drilling fluid;

(j) for each solids-additive sample obtained in step (i), washing each such solids-additive sample with a fluid having a water activity substantially less than that of water to which a cation has been added, whereby a different type of cation is used for each such n+1 sample of solids-additive type, thus resulting in n+1 washings for each of the n types of solids-additives added to the drilling fluid;

(k) repeating steps (c) and (d) for each such solids additive type;

(l) measuring the dielectric constant of each of the n+1 solids-additive samples for each of the solids-additive types added to the drilling fluid at the same preselected frequency used in steps (e) and (h);

(m) obtaining the amount of formation solids present in the drilling fluid sample and the quantities of each solids-additive type added to the drilling fluid in accordance with the following relationship, which will result in a total of m=n+1 equations and n+1 unknowns which can be resolved mathematically to obtain the amount of formation solids present in the drilling fluid sample and the quantities of each solids-additive type added to the drilling fluid:

$$DCM(ms)_j = aDCM(dc)_j + \sum_{i}^{n} b_i DCM(add_i)_j$$

where:
a is amount of solids from the formation expressed as a fraction of total solids in the drilling fluid;
DCM(ms) is the dielectric constant of the drilling fluid-solids sample obtained in step (e);
DCM(dc) is the dielectric constant of the drill cuttings sample obtained in step (h);
j is the type of cation used in step (j);
$DCM(add_i)$ is the dielectric constant of solids-additive i, i=1 to n;
n is the number of solids-additive types; and
$b_i$ is the weight factor of solids-additive type i as a fraction of the total solids weight.

7. A method for determining the content of formation solids present in water-base polymer drilling fluids, with known types of solids-additives but unknown quantities of said solids-additives, by dielectric measurements, comprising the steps of:

(a) cleaning a drilling fluid sample with a fluid having a PH in the acid range;

(b) separating the solids and liquid in the drilling fluid sample by means of centrifuging, thus creating a drilling fluid-solids sample and a drilling fluid-liquid sample;

(c) washing the drilling fluid-solids sample with fluid having a water activity substantially less than that of water to which a cation has been added;

(d) packing the washed drilling fluid-solids sample into a sample cell suitable for dielectric measurement;

(e) measuring the dielectric constant of the washed drilling fluid-solids sample at a preselected frequency;

(f) grinding a sample of drill cuttings from the same formation to a size suitable for testing;

(g) repeating the washing step (c) and the packing step (d), for the drill cuttings sample;

(h) measuring the dielectric constant of the drill cuttings sample at the same preselected frequency used in step (e);

(i) for each solids-additive type which has been added to the drilling fluid, grinding n+1 samples of each such solids-additive type to sizes suitable for testing;

(j) for each solids-additive sample obtained in step (j), washing each such solids-additive sample with a fluid having a water activity substantially less than that of water to which a cation has been added, whereby a different type of cation is used for each such n+1 sample of solids-additive type, thus resulting in n+1 washings for each of the n types of solids-additives added to the drilling fluid;

(k) repeating the washing step (c) and the packing step (d) for each such solids-additive type;

(l) measuring the dielectric constant of each of the n+1 solids-additive samples for each of the solids-additive types added to the drilling fluid the same preselected frequency used in steps (e) and (h);

(m) obtaining the amount of formation solids present in the drilling fluid sample and the quantities of each solids-additive type added to the drilling fluid in accordance with the following relationship, which will result in a total of m=n+1 equations and n+1 unknowns which can be resolved mathematically to obtain the amount of formation solids present in the drilling fluid and the quantities of each solids-additive type added to the drilling fluid:

$$DCM(ms)_j = aDCM(dc)_j + \sum_{i}^{n} b_i DCM(add_i)_j$$

where:
a is amount of solids from the formation expressed as a fraction of total solids in the drilling fluid;
DCM(ms) is the dielectric constant of the drilling fluid-solids sample obtained in step (e);
DCM(dc) is the dielectric constant of the drill cuttings sample obtained in step (h);
j is the type of cation used in step (j);
$DCM(add_i)$ is the dielectric constant of solids-additive i, i=1 to n;
n is the number of solids-additive types; and
$b_i$ is the weight factor of solids-additive type i as a fraction of the total solids weight.

8. The method of claims 1, 2, 3, 4, 5, 6, or 7 wherein said fluid is a mixture of alcohol and water.

9. The method of claims 1, 2, 3, 4, 5, 6, or 7 wherein said mixture is 70% (volume) isopropyl alcohol and 30% (volume) water.

10. The method of claims 1, 2, 3, 4, 5, 6, or 7 wherein said packing is accomplished by centrifuging the sample cell.

11. The method of claims 1, 2, 3, 4, 5, 6, or 7 wherein the preselected frequency of measurement is about 1 megahertz.

* * * * *